(12) United States Patent  
Cihlar

(10) Patent No.: US 7,071,305 B2
(45) Date of Patent: Jul. 4, 2006

(54) ISOLATED HOAT POLYPEPTIDE

(75) Inventor: Tomas Cihlar, San Mateo, CA (US)

(73) Assignee: Gilead Sciences, Inc., Foster City, CA (US)

(*) Notice: Subject to any disclaimer, the term of this patent is extended or adjusted under 35 U.S.C. 154(b) by 251 days.

(21) Appl. No.: 10/086,816

(22) Filed: Feb. 28, 2002

(65) Prior Publication Data

US 2003/0106075 A1 Jun. 5, 2003

Related U.S. Application Data

(62) Division of application No. 09/330,245, filed on Jun. 10, 1999, now Pat. No. 6,432,631.

(60) Provisional application No. 60/088,864, filed on Jun. 11, 1998, provisional application No. 60/132,267, filed on May 3, 1999.

(51) Int. Cl.
*C07K 14/00* (2006.01)

(52) U.S. Cl. .................................................. 530/350

(58) Field of Classification Search ................ 530/350
See application file for complete search history.

(56) References Cited

FOREIGN PATENT DOCUMENTS

| WO | WO 97/31111 | 8/1997 |
|---|---|---|
| WO | WO 97/42321 | 11/1997 |
| WO | WO 98/53064 | 11/1998 |

OTHER PUBLICATIONS

Pettit GR et al. Antineoplastic agents. 400. Synthesis of the Indian Ocean marine sponge cyclic heptapeptide phakellistatin 2. Nat Prod. Mar. 1999;62(3):409-14.*
Sekine T et al.,Expression cloning and characterization of a novel multispecific organic anion transporter. J Biol Chem. 1997 Ju 25;272(30):18526-9.*
Voet et al. Biochemistry. 1990. John Wiley & Sons, Inc. pp. 126-128 and 228-234.*
Mickle JE et al. Genotype-phenotype relationships in cystic fibrosis. Med Clin North Am. May 2000;84(3):597-607.*
Reid G et al. Cloning of a human renal p-aminohippurate transporter, hROAT1. Kidney Blood Press Res. 1998;21(2-4):233-7.*

Apiwattanakul et al., "Transport Properties of Nonsteroidal Anti-Inflammatory Drugs by Organic Anion Transporter 1 Expressed in Xenopus laevis Oocytes", 55:847-854, Mol Pharm, 1999.
Cihlar et al., "The Antiviral Nucleotide Analogs Cidofovir and Adefovir Are Novel Substrates for Human and Rat Renal Organic Anion Transporter 1", 56:570-580, Molecular Pharmacology, 1999.
Cundy et al., "Effect of Probenecid on the Distribution, Metabolism, and Excretion of Cidofovir in Rabbits", 24(3):315-321, The American Society for Pharmacology and Experimental Therapeutics, 1996.
Fisher et al., "Safety of adefovir dipivoxil (ADV) and Incidence of Proximal Renal Tubular Disorder (PRTD) in a Placebo (PLC)-Controlled Trial in Patients (Pt) with Advanced HIV Disease", Abstract 678, 6th Conference on Retroviruses and Opportunistic Infections, Chicago, IL, Jan. 31-Feb. 4, 1999.
Hosoyamada et al., "Molecular Cloning and functional Expression of a Multispecific Organic Anion Transporter from Human Kidney", 45(1):F122-F128, Am J Physiol, Jan. 1999.
Kuze et al., "Heterologous Expression and Functional Characterization of a Mouse Renal Organic Anion Transporter in Mammalian Cells", 274(3):1519-1524, J Biol Chem, 1999.
Lalezari et al., "Intravenous Cidofovir for Peripheral Cytomegalovirus Retinitis in Patients with AIDS", 126(4):257-263, Ann Int Med, Feb. 15, 1997.
Lopez-Nieto et al., "Molecular Cloning and Characterization of NKT, a Gene Product Related to the Organic Cation Transporter Family that is Almost Exclusively Expressed in the Kidney", 272(10):6471-6478, J Biol Chem, Mar. 7, 1997.
Lu et al., "Cloning of the human kidney PAH transporter: narrow substrate specificity and regulation by protein kinase C", 45(2):F295-F303, Am J Physiol, Feb. 1999.

(Continued)

*Primary Examiner*—Joseph Murphy
(74) *Attorney, Agent, or Firm*—Mark L. Bosse

(57) ABSTRACT

This invention is concerned with human organic anion transporter ("hOAT"). Isolated nucleic acid encoding hOAT is provided, along with ioslated hOAT polypeptide. hOAT nucleic acid and/or hOAT polypeptide are employed in transgenic animals, recombinant cells, replicable vectors and analytical procedures for identifying hOAT agonists or antagonists, assays for identifying hOAT alleles and/or isotypes, screening tests for nephrotoxic or neurologically active compounds, and determination of drug-drug interactions within the kidney or brain.

1 Claim, 3 Drawing Sheets

OTHER PUBLICATIONS

Lu et al., "Cloning of a Human Kidney P-aminohippurate (PAH) Transporter: Narrow Substrate Specificity and Regulation by Protein Kinase C", 9:54A XP002097951, Journal of the American Society of Nephrology, Sep. 9, 1998.

Mulato et al., "Nonsteroidal Anti-Inflammatory Drugs Efficiently Reduce the Transport and Cytotoxicity of Adefovir Mediated by the Human Renal Organic Anion Transporter 1", 295(1):10-15, The Journal of Pharmacology and Experimental Therapeutics, Mar. 14, 2000.

Race et al., "Molecular Cloning and Characterization of Two Novel Human Renal Organic Anion Transporters (hOAT1 and hOAT3)", 255:508-514, Biochem Biophys Res Comm, 1999.

Reid et al., "Cloning of a Human Renal p-Aminohippurate Transporter, hROAT1", 21:233-237, Kidney & Blood Pressure Research, 1998.

Rudinger, J., "Peptide Hormones", pp. 1-7, University Park Press, Baltimore, (J. A. Parsons, ed.), 1976.

Saito et al., "Cloning and Functional Characterization of a Novel Rat Organic Anion Transporter Mediating Basolateral Uptake of Methotrexate in the Kidney", 271(34):20719-20725, J Biol Chem, Aug. 23, 1996.

Sekine et al., "Expression Cloning and Characterization of a Novel Multispecific Organic Anion Transporter", 272(30):18526-18529, J Biol Chem, Jul. 25, 1997.

Sweet et al., "Expression Cloning and Characterization of ROAT1", 272(48):30088-30095, J Biol Chem, Nov. 28, 1997.

Tune, B.M., "Nephrotoxicity of beta-lactam antibiotics: mechanisms and strategies for prevention", 11:768-772, Pediatr. Nephrol., 1997.

Wolff et al., "Expression Cloning and Characterization of a Renal Organic Anion Transporter from Winter Flounder", 417(3):287-291, FEBS, 1997.

* cited by examiner

```
TTCCTGCCCTGACCCCCAAAGTGAGGAGAAGCTGCAAGGGAAAAGGGAGGGACAGATCAG
                                                              60

GGAGACCGGGGAAGAAGGAGGACGAGCCAAGGAGGCTGCTGTCCCCCCACAGAGCAGCTC
                                                              120

GGACTCAGCTCCCGGGAAGCAACCCAGCTGCGGAGGCAACGGCAGTGCTGCTCCTCCAGC
                                                              180

GAAGGACAGCAGGCAGGCAGACAGACAGAGGTCCTGGGACTGGAAGGCCTCAGCCCCCAG
                                                              240

CCACTGGGCTGGGCCTGGCCCAATGGCCTTTAATGACCTCCTGCAGCAGGTGGGGGGTGT
                                                              300
                    M   A   F   N   D   L   L   Q   Q   V   G   G   V

CGGCCGCTTCCAGCAGATCCAGGTCACCCTGGTGGTCCTCCCCCTGCTCCTGATGGCTTC
                                                              360
 G   R   F   Q   Q   I   Q   V   T   L   V   V   L   P   L   L   L   M   A   S

TCACAACACCCTGCAGAACTTCACTGCTGCCATCCCTACCCACCACTGCCGCCCGCCTGC
                                                              420
 H   N   T   L   Q   N   F   T   A   A   I   P   T   H   H   C   R   P   P   A

CGATGCCAACCTCAGCAAGAACGGGGGGCTGGAGGTCTGGCTGCCCCGGGACAGGCAGGG
                                                              480
 D   A   N   L   S   K   N   G   G   L   E   V   W   L   P   R   D   R   Q   G

GCAGCCTGAGTCCTGCCTCCGCTTCACCTCCCCGCAGTGGGGACTGCCCTTTCTCAATGG
                                                              540
 Q   P   E   S   C   L   R   F   T   S   P   Q   W   G   L   P   F   L   N   G

CACAGAAGCCAATGGCACAGGGGCCACAGAGCCCTGCACCGATGGCTGGATCTATGACAA
                                                              600
 T   E   A   N   G   T   G   A   T   E   P   C   T   D   G   W   I   Y   D   N

CAGCACCTTCCCATCTACCATCGTGACTGAGTGGGACCTTGTGTGCTCTCACAGGGCCCT
                                                              660
 S   T   F   P   S   T   I   V   T   E   W   D   L   V   C   S   H   R   A   L

ACGCCAGCTGGCCCAGTCCTTGTACATGGTGGGGGTGCTGCTCGGAGCCATGGTGTTCGG
                                                              720
 R   Q   L   A   Q   S   L   Y   M   V   G   V   L   L   G   A   M   V   F   G

CTACCTTGCAGACAGGCTAGGCCGCCGGAAGGTACTCATCTTGAACTACCTGCAGACAGC
                                                              780
 Y   L   A   D   R   L   G   R   R   K   V   L   I   L   N   Y   L   Q   T   A
```

FIG. 1

```
TGTGTCAGGGACCTGCGCAGCCTTCGCACCCAACTTCCCCATCTACTGCGCCTTCCGGCT
                                                              840
 V  S  G  T  C  A  A  F  A  P  N  F  P  I  Y  C  A  F  R  L

CCTCTCGGGCATGGCTCTGGCTGGCATCTCCCTCAACTGCATGACACTGAATGTGGAGTG
                                                              900
 L  S  G  M  A  L  A  G  I  S  L  N  C  M  T  L  N  V  E  W

GATGCCCATTCACACACGGGCCTGCGTGGGCACCTTGATTGGCTATGTCTACAGCCTGGG
                                                              960
 M  P  I  H  T  R  A  C  V  G  T  L  I  G  Y  V  Y  S  L  G

CCAGTTCCTCCTGGCTGGTGTGGCCTACGCTGTGCCCCACTGGCGCCACCTGCAGCTACT
                                                              1020
 Q  F  L  L  A  G  V  A  Y  A  V  P  H  W  R  H  L  Q  L  L

GGTCTCTGCGCCTTTTTTTGCCTTCTTCATCTACTCCTGGTTCTTCATTGAGTCGGCCCG
                                                              1080
 V  S  A  P  F  F  A  F  F  I  Y  S  W  F  F  I  E  S  A  R

CTGGCACTCCTCCTCCGGGAGGCTGGACCTCACCCTGAGGGCCCTGCAGAGAGTCGCCCG
                                                              1140
 W  H  S  S  S  G  R  L  D  L  T  L  R  A  L  Q  R  V  A  R

GATCAATGGGAAGCGGGAAGAAGGAGCCAAATTGAGTATGGAGGTACTCCGGGCCAGTCT
                                                              1200
 I  N  G  K  R  E  E  G  A  K  L  S  M  E  V  L  R  A  S  L

GCAGAAGGAGCTGACCATGGGCAAAGGCCAGGCATCGGCCATGGAGCTGCTGCGCTGCCC
                                                              1260
 Q  K  E  L  T  M  G  K  G  Q  A  S  A  M  E  L  L  R  C  P

CACCCTCCGCCACCTCTTCCTCTGCCTCTCCATGCTGTGGTTTGCCACTAGCTTTGCATA
                                                              1320
 T  L  R  H  L  F  L  C  L  S  M  L  W  F  A  T  S  F  A  Y

CTATGGGCTGGTCATGGACCTGCAGGGCTTTGGAGTCAGCATCTACCTAATCCAGGTGAT
                                                              1380
 Y  G  L  V  M  D  L  Q  G  F  G  V  S  I  Y  L  I  Q  V  I

CTTTGGTGCTGTGGACCTGCCTGCCAAGCTTGTGGGCTTCCTTGTCATCAACTCCCTGGG
                                                              1440
 F  G  A  V  D  L  P  A  K  L  V  G  F  L  V  I  N  S  L  G

TCGCCGGCCTGCCCAGATGGCTGCACTGCTGCTGGCAGGCATCTGCATCCTGCTCAATGG
                                                              1500
 R  R  P  A  Q  M  A  A  L  L  L  A  G  I  C  I  L  L  N  G

GGTGATACCCCAGGACCAGTCCATTGTCCGAACCTCTCTTGCTGTGCTGGGGAAGGGTTG
                                                              1560
 V  I  P  Q  D  Q  S  I  V  R  T  S  L  A  V  L  G  K  G  C
```

FIG. 2

```
TCTGGCTGCCTCCTTCAACTGCATCTTCCTGTATACTGGGGAACTGTATCCCACAATGAT
                                                              ─ 1620
  L   A   A   S   F   N   C   I   F   L   Y   T   G   E   L   Y   P   T   M   I

CCGGCAGACAGGCATGGGAATGGGCAGCACCATGGCCCGAGTGGGCAGCATCGTGAGCCC
                                                              ─ 1680
  R   Q   T   G   M   G   M   G   S   T   M   A   R   V   G   S   I   V   S   P

ACTGGTGAGCATGACTGCCGAGCTCTACCCCTCCATGCCTCTCTTCATCTACGGTGCTGT
                                                              ─ 1740
  L   V   S   M   T   A   E   L   Y   P   S   M   P   L   F   I   Y   G   A   V

TCCTGTGGCCGCCAGCGCTGTCACTGTCCTCCTGCCAGAGACCCTGGGCCAGCCACTGCC
                                                              ─ 1800
  P   V   A   A   S   A   V   T   V   L   L   P   E   T   L   G   Q   P   L   P

AGACACGGTGCAGGACCTGGAGAGCAGGAAAGGGAAACAGACGCGACAGCAACAAGAGCA
                                                              ─ 1860
  D   T   V   Q   D   L   E   S   R   K   G   K   Q   T   R   Q   Q   Q   E   H

CCAGAAGTATATGGTCCCACTGCAGGCCTCAGCACAAGAGAAGAATGGACTCTGAGGACT
                                                              ─ 1920
  Q   K   Y   M   V   P   L   Q   A   S   A   Q   E   K   N   G   L

GAGAAGGGGCCTTACAGAACCCTAAAGGGAGGGAAGGTCCTACAGGTCTCCGGCCACCCA
                                                              ─ 1980

CACAAGGAGGAGGAAGAGGAAATGGTGACCCAAGTGTGGGGGTTGTGGTTCAGGAAAGCA
                                                              ─ 2040

TCTTCCCAGGGGTCCACCTCCCTTTATAAACCCCACCAGAACCACATCATTAAAAGGTTT
                                                              ─ 2100

GACTGCGAAAAAAAAAAAAAAAA
                        → 2123
```

ISOLATED HOAT POLYPEPTIDE

This application is a Divisional of Ser. No. 09/330,245 filed Jun. 10, 1999, now U.S. Pat. No. 6,432,631, which claims benefit of 60/088,864 filed Jun. 11, 1998, and claims benefit of 60/132,267 filed May 03, 1999.

BACKGROUND OF THE INVENTION

This invention relates to the processing of anions by the human kidney. In particular, it relates to nucleic acids and polypeptides transcribed and expressed in the kidneys that are responsible for the removal of toxic anions from the circulation.

Sweet et al. have described a rat gene (ROAT1) encoding an organic anion transport protein expressed in the rat kidney (*Journal of Biological Chemistry* 272:30088–30095 [1997]). Sekine et al. also appear to have disclosed essentially the same gene, denominated OAT1 (*Journal of Biological Chemistry* 272:18526–18529 [1997]). Its apparent murine counterpart has been described in Lopez-Nieto et al. *Journal of Biological Chem.* 272:6471–6478 (1997).

It is an object of this invention to isolate nucleic acid encoding a human organic anion transporter (hOAT).

It is another object of this invention to recombinantly express nucleic acid encoding hOAT.

Another object is to obtain hOAT expressed in elevated yields in recombinant cell culture.

An object is to prepare isolated polypeptide encoding hOAT.

An additional object of this invention is to provide novel hOAT polypeptides.

A further object of this invention is an assay for evaluation of potential drug-drug interactions due to interference of one drug or group of drugs with hOAT-mediated active kidney excretion of another drug.

A further object of this invention is an assay system for screening candidate compounds that agonize or antagonize the expression of hOAT and/or the biological activity of hOAT polypeptide, especially its anion transport activity.

Another object is to provide an hOAT screening assay system to identify molecular variants of nephrotoxic compounds that will be taken up and transported by hOAT to a lesser degree than is the case with the parental compound.

A further object is to identify alleles or isoforms of hOAT that are associated with sensitivity to nephrotoxic compounds, particularly nephrotoxic drugs.

These and other objects of the invention will be apparent from consideration of this specification as a whole.

SUMMARY OF THE INVENTION

In accordance with the objects, applicants provide isolated nucleic acid encoding hOAT and isolated hOAT polypeptide. hOAT is expressed in recombinant cells, where it finds use in evaluating compounds for nephrotoxicity or for identifying compounds having the ability to prevent nephrotoxicity. Since hOAT is expressed in human brain, it also finds use in characterizing compounds known or suspected to influence brain function. hOAT also is useful in a method for identifying any hOAT alleles and isoforms which are correlated with patient sensitivity to nephrotoxic agents.

BRIEF DESCRIPTION OF THE DRAWINGS

FIGS. 1–3 depict a nucleotide sequence for cDNA encoding hOAT (SEQ. ID No. 1) and its translated sequence (SEQ. ID No. 2). FIG. 1 depicts the first 780 nucleotides of the sequence. FIG. 2 depicts nucleotides 781-1560 of the sequence. FIG. 3 depicts nubleotides 1561-2123 of the sequence.

DETAILED DESCRIPTION OF THE INVENTION hOAT polypeptide is defined as a polypeptide sequence that is at least about 85% homologous by amino acid sequence (ordinarily at least about 90%, and prefereably at least about 95%) with the sequence of FIG. 1 (reference sequence hOAT).

An expressed sequence tag (EST) of approximately 200 bp having high homology to a segment of hOAT is found in the GenBank EST entries under accession no. R25797. Invention hOAT nucleic acids per se as defined herein exclude any expressed sequence tag (EST) or other nucleic acid sequences found in public databases on the filing date (such databases being expressly incorporated by reference), including the sequence of accession no. R25797 as well as the rat ROAT1 and OAT1, and mouse NKT, sequences of the prior art. However, other inventive subject matter such as isolated protein, methods for screening and the like as set forth above do not (unless expressly stated to the contrary) exclude the use of the R25797 sequence or its expression product.

"Homology" is defined as the percentage of residues in a candidate amino acid sequence that is identical with the residues in the reference sequence hOAT after aligning the two sequences and introducing gaps, if necessary, to achieve the maximum percent homology. Methods and computer programs for the alignment are well know in the art. One computer program which may be used or adapted for purposes of determining whether a candidate sequence falls within this definition is "Align 2", authored by Genentech, Inc., which was filed with user documentation in the United States Copyright Office, Washington, D.C. 20559, on Dec. 10, 1991.

"Isolated" hOAT nucleic acid is one that has been separated from its environment as it is found in nature, i.e., from the genome in the case of DNA or from cellular environment in the instance of RNA.

"Isolated" hOAT polypeptide is one that has been separated from its normal cellular environment, and includes hOAT protein that is homogeneous by SDS-PAGE using silver stain.

In calculating amino acid sequence homology the candidate and reference sequences are aligned in the fashion that produces the maximum number of aligned residues, with insertions and deletions of residues represented by gaps in the aligned sequences. For example, a 120 residue polypeptide containing a 100 residue reference sequence fragment fused at its N-terminus to a 6 residue polyhistidine affinity tag, but with a single substitution in the hOAT domain, is calculated to be 99% homologous to the hOAT reference sequence since the sequence of the fragment corresponds exactly to the maximally aligned hOAT reference sequence except for a single residue substitution and the 6 residue N-terminal fusion. Thus, if the alignment-maximizing comparison of the candidate and reference sequences reveals an insertion (or deletion) of one or more amino acid residues, then these residues are ignored for the purposes of making the homology calculation. Applicant recognizes that this convention gives rise to theoretical 100% homology between 2 differing sequences, but has chosen to establish his own definition for the purposes of this filing.

Analysis of homology is based on any one or more of the sequences imputed from the nucleic acid used to express the hOAT, the sequence of the product as first produced in vitro, or the sequence after any post-translational modification. Thus, if the reference and candidate sequences are identical when expressed, but a glutamine residue is later deaminated to glutamic acid, the first candidate is 100% homologous, but the deaminated sequence is not.

For the purposes herein "hOAT activity" means any one or more of the functions performed by hOAT in the human, including in particular the transport of organic anions.

It is not necessary for a polypeptide to have anion transport activity in order to fall under the definition of hOAT herein. For example, in some embodiments hOAT polypeptides possess at least one immune epitope that is capable of substantial cross-reaction with an antibody raised against reference sequence hOAT, and thus are useful in immunoassays for hOAT, but may possess mutations that render the polypeptide incapable of anion transport.

The hOAT polypeptides of this invention comprise substitutions for, deletions of, or insertions of any amino acid residue adjacent to any of the reference sequence amino acid residue sites shown in FIG. 1. Substitutional hOATs are those in which at least one amino acid residue in the reference sequence has been removed and a different amino acid inserted in its place at the same position. One or more residues are substituted.

Alanine is a common substitution for any residue, and is commonly used in alanine scanning to identify functional residues, but it is within the scope of this invention to substitute other residues into the hOAT reference sequence. The introduced residues generally are naturally occurring amino acids, commonly G, A, Y, V, L, I, S, T, D, E, Q, C, M, N, F, P, W, K, R or H (using conventional single letter code; EP 323,149). Suitable residues also include hydroxyproline, beta-hydroxyaspartic acid, gamma-carboxyglutamic acid, hydroxylysine or norleucine, to be employed as alternatives to their namesakes.

These substitutions may be conservative, i.e., the substituting residue is structurally or functionally similar to the substituted residue. Other substitutions will be less conservative in that they constitute an exchange between different structural or functional classes of residues. For the purposes herein, these classes are as follows: 1. Electropositive: R, K, H; 2. Electronegative: D, E; 3. Aliphatic: V, L, I, M; 4. Aromatic: F, Y, W; 5. Small: A, S, T, G, P, C; 6. Charged: R, K, D, E, H; 7. Polar: S, T, Q, N, Y, H, W; and 8. Small Hydrophilic: C, S, T. Intergroup substitutions generally will have greater effects on protein function than conservative (intraclass) substitutions. Thus, it is particularly within the scope of this invention to introduce conservative substitutions into hOAT and, if the results are not satisfactory, to introduce non-conservative substitutions at the sites. Typically, however, proline, glycine, and cysteine substitutions or insertions into the sequence are not favored. An example of an expressed variant is a change at codon 498 from AGC to ATC, resulting in expression of isoleucine in place of serine. Other variants are introduced into DNA encoding hOAT without resulting in a change in protein sequence, e.g. from ATC to ATT at codon 453 or from GGG to GGT at codon 491.

hOAT variants are readily identified by methods apparent to the ordinary artisan. For example, sites shown by alanine scanning to influence selected biological activity are subjected to saturation mutagenesis to identify the optimal modification for the activity in question, e.g. selectivity for transport of a particular anion.

hOATs representing combinations of sequence variants are within the scope of this invention. 2, 3, 4, 5, or more substitutions, deletions or insertions are introduced into hOAT as defined herein. Typically, a deletion of a single residue will be accompanied by an insertion within 1 to about 3 residues of the deletion site. Generally, deletions of larger domains unnecessary for anion transport activity need not be accompanied by an insertion. The results of individual amino acid substitutions are generally additive except when the residues interact with each other directly or indirectly. They are readily screened using the same procedures described in Sweet et al. or Sekine et al. (supra) in order to identify those having the properties of reference sequence hOAT or the desired modified properties.

Included within the scope of this invention are hOATs having one or more amino acids inserted immediately adjacent to a hOAT amino acid at any position in the reference sequence. Insertional hOATs generally will have a polypeptide structure comprising the sequence $NH_2$-PP-A-$(X)_{n1}$-B-PP-COOH, wherein X is the inserted residue(s) (which may be the same or different), n1 is an integer (generally 1–30, typically 1 or 2), either A or B are the designated residue sites for insertion and PP represents the remainder of the hOAT or a bond at the hOAT N or C terminus.

The invention includes fusions of hOAT and selected antibody recognition sequences (heterologous polypeptides) for immunoaffinity purification of hOAT from cell culture, fusions of hOAT sequences with affinity tags such as FLAG or polyhistidine, and chimeric sequences (particularly fusions of hOAT sequence fragments with fragments of other receptors of the 12-transmembrane spanning region class).

Also included within the scope of this invention are hOATs in which a glycosylation site is introduced or removed from the reference sequence, whether by substitution, insertion or deletion of one or more amino acid residues. Such changes will result in the installation or removal of the sequence NXS or NXT, where X can be any residue. Thus, asparagine can be substituted for any residue located 2 residues N-terminal to serine or threonine to introduce a glycosylation site. Alternatively, single glycosylation can be omitted by substituting glycosylated asp with any residue, deleting site-adjacent serine or threonine substituting any residue into the glycosylation site to perturb the NXS or NST sequence.

Also included within the scope of this invention are deletional hOATs, i.e., hOATs in which one or more amino acid residues of the reference sequence have been removed at a designated site, whereby flanking residues are now joined by a peptide bond in the ordinary fashion. It generally is not preferred to delete P, C or G residues.

Typically, deletions or insertions are relatively small, on the order of 1 to 10 residues and generally no more than 2, although deletions or insertions can be quite large if they are not in critical portions of the reference sequence, or the additional sequence is to be removed at some point during post-translational or post-recovery processing. The number of residues that are deleted or inserted in part will depend upon whether or not they are found in secondary structural components such as helices or sheets (whereupon only 1 or, preferably 2 residues are inserted or deleted), or are in less structurally confined domains such as loops, where larger numbers of residues may be deleted or inserted without unduly perturbing the structure of hOAT.

The hOATs of this invention may be subject to post-translational covalent modification, e.g. deamidation of asparagine or glutamine, or oxidation of cysteine residues.

Glycosylation can be variant or absent depending upon the host cell used to express the variant. hOATs containing such modifications are included within the scope of this invention. If hOAT is glycosylated in recombinant cell culture, it preferably is glycosylated with carbohydrates characteristic of mammalian cells, although it also may bear fungal (such as yeast) glycosylation patterns. Glycosylation is acceptable which is characteristic of expression of hOAT from one or more of fibroblast, kidney, brain, lung, skin, neural, liver or bone marrow cells or cell lines, or from any mammalian cell line such as CHO or embryonic kidney cells.

Naturally occurring human alleles are included within the scope of this invention. These readily are identified by obtaining nucleic acid samples from individuals in a population, sequencing hOAT from such individuals and determining residues at which variation is found. Once each variation is identified, it is straight-forward to determine the frequency of the putative allele in other individuals by PCR using primers specific for the domain in question, or such other methods as are conventional in the field for determining proportions of alleles in human populations.

Preparation of hOAT Polypeptides

The hOATs of this invention are readily prepared by methods known in the art. In general, nucleic acid encoding the hOAT is prepared by PCR, by in vitro synthesis (Vasser et al., "N.A.R." 18(a0):3089 [1990]), by cloning from a human genomic or kidney cDNA library or combinations thereof. Site-directed mutagenesis of hOAT-encoding nucleic acid is used to prepare nucleic acid encoding sequence variants. The + (coding) and − strands (antisense) of hOAT are included within the scope of hOAT nucleic acids, as are hOAT-encoding cDNA, genomic DNA and RNA. hOAT DNA includes 5' and 3' regions of the hOAT gene that are not transcribed but serve as transcription control domains, and transcribed but not expressed domains such as introns (including splice junctions), polyadenylation signals, ribosomal recognition domains and the like.

The hOAT nucleic acid is expressed in in vitro systems or in recombinant host cells. One method for expression is ribosome based synthesis using dedicated tRNAs (Benner, "TIBTECH" 12:158–163 [1994] and Robertson et al., "J. Am. Chem. Soc." 113:2722–2729 [1991]). Ordinarily, however, the hOAT-encoding nucleic acid (generally DNA) is inserted into an appropriate expression vector recognized (transcribed and translated) by the host cells, host cells are transfected with the expression vector, the recombinant host cells are grown in suitable culture medium, and optionally the desired hOAT is recovered from the recombinant cell culture by chromatographic or other purification methods. It is also within the scope of this invention to partially synthesize the hOAT in recombinant cell culture or by in vitro methods and then ligate the polypeptide fragments by peptide ligase (reverse proteolytic synthesis).

The nucleic acid for expression of the hOAT may comprise an exogenous signal sequence. Here, the hOAT is expressed as a preprotein of hOAT, whereby the hOAT is expressed as a precursor that is processed to mature hOAT. Suitable presequences include those of (a) microbial proteases such as subtilisin, (b) mammalian polypeptides, (c) cytokines such as gamma interferon or an interleukin, (d) growth factors such as growth hormone or TGF-alpha, (e) polypeptides or proteins having N-terminal mature sequences that are homologous to human hOAT, (f) immunoglobulins, (g) receptors, or (h) other presequences of secreted or cell membrane bound proteins. Signal sequences optionally are derived from or are homologous to the host cell, or at least the phylogenetic branch to which the host cell belongs. For example, one ordinarily would use a presequence of a yeast protein, such as mating factor, in a yeast expression system, or of a bacterium, such as ST-II or beta-lactamase, in bacterial cell culture systems. A wide variety of suitable signal sequences are known and can be used in methods for the preparation of the hOATs described herein.

The nucleic acid constructs encoding hOAT generally are spliced into expression vectors where they will be under the control of sequences controlling transcription, translation and RNA stability. These sequences include promoters, operators, enhancers and polyadenylation sequences, and are generally known in the art. Constructing suitable expression vectors for hOATs of this invention is a matter of routine for those skilled in the art, and will be accomplished using the conventional tools of molecular biology, including nucleic acid synthesis in vitro, PCR, adapters, ligases, restriction enzymes, expression and shuttle plasmids, transfection aids and the like, all of which are publicly (and for the most part commercially) available.

Suitable host cells for transfection with nucleic acid encoding hOAT are well known. Some are mentioned above while others are described in WO 93/13208 at page 12, line 21–page 19, line 5, and EP 319,312 B1, page 16, lines 10–18 and Table II thereof. It may be optimal to use host cells that are capable of glycosylating hOAT, typically including mammalian cells such as embryonic kidney 293 cells, COS cells, CHO, BHK-21 cells and the like. *Xenopus* oocytes are suitable for expression of hOAT RNA. In addition, host cells that have been used heretofore to express anion transporter polypeptides in recombinant cell culture are suitable.

The host-vector system should yield substantially homogeneous hOAT, thereby avoiding the need to purify various hOAT alleles, isoforms or cleavage products from one another. If the host cell is capable of glycosylation, essentially all of the hOAT molecules should be glycosylated. In addition, host cells optimally will not proteolyse hOAT. Cells can be selected that contain no protease, e.g., in the periplasm, that will cleave hOAT. For example, *E. coli* and other microbial strains are known that possess little or no extracellular or periplasmic proteolytic activity (other than signal peptidases). The absence of deleterious proteases helps to ensure that the product is not rendered microheterogenous as to chain length by host-endogenous proteases acting on the hOAT expression product. In addition, or alternatively, basic residues of hOAT that define sites for proteolytic cleavage are substituted with residues other than K or R.

The hOAT recombinant cells are cultured under conventional conditions using conventional culture media heretofore employed with the cells in question. These conditions and media are widely known. Freshly transfected cells may only transiently express the hOATs, but stable transformants readily are obtained in accord with conventional practice using cotransformation with a selection gene such as DHFR or glutamine synthetase and serial culture in the presence of a selection agent such as methotrexate or methionine sulfoximine, respectively. Yields of hOATs can differ substantially despite minor differences in the character of substituents or insertions. In such cases, it is desirable to screen for an expression system that will yield a quantity of hOAT that is at least about 75% of that obtained with the reference hOAT in the same expression system.

The hOAT may be expressed in bacteria in the form of retractile bodies, in which base the insoluble hOAT is recovered and refolded using known methods, e.g. dissolution in a denaturant such as guanidinium hydrochloride followed by gradual removal of the denaturant. Directly expressed hOATs of this invention may have an extra N-terminal methionine or blocked methionine residue, although host cells can be employed that will cleave away such N-terminal methionine residues if they are extraneous to the protein as found in nature. In order to avoid difficulties with insoluble expression products it is preferable to express hOAT in eukaryotic, more preferably mammalian, cells.

hOAT is isolated or purified from recombinant cell culture by methods heretofore employed for other proteins, e.g., native or reducing/SDS gel electrophoresis, isoelectric focusing, immobilized pH gradient electrophoresis, salt precipitation, solvent fractionation (using ethanol for example) and chromatography such as gel filtration, ion exchange (cation or anion), ligand affinity (cibacron blue F3GA or p-aminobenzamidine), immunoaffinity, chromatofocusing, reverse phase or hydrophobic interaction chromatography. Typically, the hOAT will be isolated so as to be >95% pure by weight of protein, and preferably greater than 99% pure. However, the term "isolated" as used in reference to hOAT protein or nucleic acid refers to the absence of one or more of the normal human polypeptides or nucleic acids found in association with hOAT in its natural environment, and does not necessarily imply that the hOAT is purified to any degree free of non-hOAT proteins. Since hOAT is normally found in the cell membrane, it is preferable to recover recombinant hOAT as a membrane preparation; otherwise the function of hOAT may be perturbed. In any case, many utilities for hOAT do not require purification of the protein at all; screening assays for agonists or antagonists are best conducted in intact host cells.

The hOAT polypeptides or their fragments optionally are prepared in vitro, especially if they are relatively small, e.g. on the order of about 30 residues or less. For example, hOATs are prepared by synthesis using standard solid-phase peptide synthesis procedures as described by Merrifield "J. Am. Chem. Soc." 85:2149 (1963). These then are ligated together by the use of peptide ligase reverse proteolysis). In vitro methods of protein synthesis also are used to prepare hOATs without the need for recombinant cell culture. Such methods are useful for small-scale preparations, and have the advantage of reducing the possible effect on yields of host cell proteases. In vitro hOAT protein synthesis has one additional quite substantial advantage in that it permits the site-specific introduction into the hOAT of a non-naturally occurring amino acid residue. Accordingly, when the term "amino acid residue" is used herein (in connection with hOAT modification by substitution or insertion, especially by a single amino acid) it will be understood that the amino acid is not limited to the naturally occurring residues associated with native tRNAs. Aminoacyl tRNA is efficiently prepared using a variety of non-naturally occurring amino acid residues ("non-naturally occurring" means not naturally found in proteins, although the amino acid might be found elsewhere in nature). Since the tRNA is selected to be incorporated at a codon not recognized by any of the tRNAs normally involved in protein synthesis, the selected non-naturally occurring amino acid residue is incorporated only at the particular site in the hOAT sequence chosen for the unique codon. Thus, in these cases the hOAT is encoded by a nucleic acid having a nonsense codon, e.g., UAG, at the desired unique insertion or substitution site.

Suitable non-naturally occurring amino acids are described for example in Greenstein et al., "Chemistry of the Amino Acids" Vols. 1–3, 1986. In general, one will use pharmaceutically innocuous L-amino acids that are found in nature but ordinarily not incorporated into proteins. Such amino acids typically will be structurally related to a naturally occurring residue that produces the desired effect at a given site and will be used to further resolve and optimize the desired property of the hOAT.

The hOATs of this invention also include hOATs that have been substituted by a non-peptidyl moiety, either for purposes of preparing the hOAT to begin with or as a subsequent modification of the hOAT prepared by amino acid substitution, insertion or deletion as described elsewhere herein. Covalent modification may accomplish essentially the same objective as a site-directed mutant at the same location using a naturally occurring residue.

Tryptophan is a relatively rare amino acid in hOAT. Accordingly, this residue is an attractive site for post-translational convalent modification because substitution at other sites is expected to be less than may be the case with more common residues. Reaction of trp with an oxidant such as a halogen donor, e.g. bromine, will yield the side chain structure

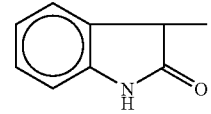

This reaction should be conducted in aqueous solvent and at low halogen concentrations.

Other covalent modifications of hOATs will be apparent to the artisan. Sensitive side chains are protected by masking them with antibodies directed against an epitope that includes the residue to be protected. Reagents for accomplishing such modifications are well-known and have been widely used in the diagnostic and preparative fields. See T. Creighton, *Proteins: Structure and Molecular Properties*, 1983.

hOATs are cross-linked to a water insoluble matrix or incorporated into a lipid vehicle such as a liposome, usually a ULV. Cross-linking is accomplished by reacting the hOAT and matrix with a bifunctional agent. Examples of suitable bifunctional agents include 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dethiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, hOAT is immobilized on reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440.

hOATs also are covalently modified by linking the hOAT to various nonproteinaceous polymers, e.g., polyethylene glycol (PEG), polypropylene glycol or polyoxyalkylenes, in the manner set forth for example in U.S. Pat. Nos. 4,640, 835; 4,496,689; 4,301,144; 4,670,417; 4,791,192 or 4,179, 337. PEG is a non-immunogenic, linear, uncharged polymer with three water molecules per ethylene oxide unit. See Maxfield, et al., "Polymer" 16:505–509 (1975); Bailey, F. E. et al., in "Nonionic Surfactants", Schick, M. J., ed, pp. 794–821 (1967). Several therapeutic enzymes have been conjugated to PEG to increase their in vivo half-life (Abuchowski, A., et al., "J. Biol. Chem." 252:3582–3586 (1977); Abuchowski, A. et al., "Cancer Biochem. Biophys." 7:175–186 (1984). An IL-2 (interleukin-2)-PEG conjugate has been reported to increase circulatory life and potency (Katre, N. V. et al., "Proc. Natl. Acad. Sci." 84:1487–1491 (1987); Goodson, R. et al., "Bio/Technology" 8:343–346 (1990)). See also Abuchowski, A. et al., "J. Biol. Chem." 252:3578–3581 (1977). Any of the methods for PEG conjugation used in these citations is acceptable for use with the hOATs of this invention.

Uses for the hOATs of this Invention

The hOATs of this invention are useful in therapeutic, diagnostic and preparatory methods. Their use will depend upon the properties that they possess, as will be apparent to the ordinary artisan. For the most part, all of the hOATs will retain hOAT immune epitopes, so they are useful in place of hOAT in hOAT immunoassays whether or not they possess any anion transport activity.

The hOATs of this invention are useful in identifying substances that bind to hOAT (hOAT binding partners, or "TBP"). Of particular interest are substances that are capable of binding to hOAT to substantially inhibit the anion transport activity of hOAT, or, preferably, to introduce favorable selectivity into the transport activity such that nephrotoxic drugs such as amphotericin or cidofovir are not taken up as avidly as in the absence of the substance. TBP's ability to bind to hOAT also is useful in methods for recovering hOAT from contaminated mixtures such as cell culture supernatants of recombinant hOAT-expressing cells (including the hOAT amino acid sequence hOATs herein). Typically, hOATs can be used in place of hOAT standards in immunoassays for hOAT if they possess at least one hOAT epitope recognized by the antibody used in the hOAT immunoassay in question, while the TBPs are used in place of antibodies for hOAT. The hOATs also are useful, as appropriate, in functional assays for certain individual properties of hOAT.

Peptide TBPs are obtained by the use of in vitro directed evolutionary methods such as those employing filamentous phage to present candidate sequences (otherwise known as phage display) and similar methods known per se which rely on the systematic generation and screening of peptides for activity. These typically are rather small molecules, containing on the order of about 5 to 20 residues.

Antibody TBPs are immunoglobulins, ordinarily monoclonal antibodies, which (in preferred embodiments) are capable of specifically inhibiting the transport function of hOAT. Antibodies are raised in conventional fashion by immunizing an animal with an immunogenic hOAT conjugate, e.g. hOAT crosslinked to keyhole limpet hemocyanin.

The term "monoclonal antibody" as used herein refers to an antibody obtained from a population of substantially homogeneous antibodies, i.e. the individual antibodies comprising the population are essentially identical in specificity and affinity. Monoclonal antibodies include hybrid and recombinant antibodies (e.g. "humanized" antibodies) regardless of species of origin or immunoglobulin class or subclass designation, as well as antibody fragments (e.g., Fab, F(ab')$_2$, and Fv). Thus, "monoclonal" antibodies are produced by any particular method that will yield a substantially homogeneous population. For example, monoclonal antibodies may be made using the methods described by Kohler & Milstein, "Nature" 256:495 (1975), Goding, *Monoclonal Antibodies: Principles and Practice* pp. 59–103 (1986), Kozbor, "J. Immunol." 133:3001 (1984), or Brodeur, et al., *Monoclonal Antibody Production Techniques and Applications*, pp. 51–63 (1987), or may be made by recombinant DNA methods. Cabilly, et al., U.S. Pat. No. 4,816,567.

In a preferred embodiment of the invention, the monoclonal antibody will have an affinity for reference sequence hOAT of at least about $10^9$ moles/liter, as determined, for example, by the Scatchard analysis of Munson & Pollard, "Anal. Biochem." 107:220 (1980). Also, the monoclonal antibody typically will inhibit the transport activity of hOAT (using a standard organic anion such as para-aminohippurate) by at least about 50%, preferably greater than 80%, and most preferably greater than 90%, as determined by conventional methods.

DNA encoding the monoclonal antibody is readily isolated and sequenced using conventional procedures (e.g., by using oligonucleotide probes that are capable of binding specifically to genes encoding the heavy and light chains of murine antibodies). Hybridoma cells serve as a preferred source of such DNA. Once isolated, the DNA may be placed into expression vectors, which are then transfected into host cells such as simian COS cells, Chinese Hamster ovary (CHO) cells, or myeloma cells that do not otherwise produce immunoglobulin protein, to obtain the synthesis of monoclonal antibodies in the recombinant host cells.

The DNA optionally may be modified in order to change the character of the immunoglobulin produced by its expression. For example, humanized forms of murine antibodies are produced by substituting a complementarity determining region (CDR) of the murine antibody variable domain for the corresponding region of a human antibody. In some embodiments, selected framework region (FR) amino acid residues of the murine antibody also are substituted for the corresponding amino acid residues in the human antibody. Humanized forms of murine antibodies also may be produced by substituting the coding sequence for human heavy and light constant chain domains in place of the homologous murine sequences. Morrison, et al., "PNAS" 81:6851 (1984).

TBP also includes nucleic acid sequences that bind hOAT. Evolutionary selection methods for oligonucleotides that bind to target proteins are well known (WO 92/14843; Ellington et al., "Nature" 355:850 (1992); Bock et al., "Nature" 355:564 (1992); Ellington et al., "Nature" 346:818 (1990); Tuerk et al., "Science" 249:505 (1990). These oligonucleotides, commonly known as aptamers, generally contain the usual A, T, G, C or U bases or derivatives thereof, and comprise sequences that bind to a predetermined site on a target protein. A selection method for TBPs that inhibit the transport function of hOAT comprises (a) preparing a pool of candidates (oligonucleotides, peptides, extracts, proteins, etc.), (b) contacting the candidates with hOAT having anion transport activity (typically reference sequence hOAT) (c) isolating from the hOAT those candidates that are able to bind to hOAT, (d) contacting the candidates from step c) with an hOAT in which the hOAT transport function has been mutated substantially out of the hOAT, and (e) recovering those candidates that do not bind to the mutated form.

For diagnostic applications, the hOATs of this invention optionally are labeled with a detectable moiety, either in vivo or in vitro. The detectable moiety can be any substituent which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; a radioactive isotopic label, such as, $^{125}$I, $^{32}$P, $^{14}$C, or $^{3}$H, or an enzyme, such as alkaline phosphatase, beta-galactosidase or horseradish peroxidase.

Any method known in the art per se can be used to conjugate the hOAT to the detectable moiety. See the methods described supra and Hunter, et al., "Nature" 144: 945 (1962); David, et al., "Biochemistry" 13:1014 (1974); Pain, et al., "J. Immunol. Meth." 40:219 (1981); and Nygren, J. "Histochem. and Cytochem." 30:407 (1982). Oligonucleotide TBPs are labeled in the conventional fashion heretofore employed in the diagnostic probe art.

The TBPs or hOATs of the present invention optionally are employed in known immunoassay techniques, such as competitive binding assays, direct and indirect sandwich assays, and immunoprecipitation assays. Zola, *Monoclonal Antibodies: A Manual of Techniques*, pp. 147–158 (1987).

Competitive binding assays rely on the ability of a labeled standard (which may be hOAT, or an immunologically reactive portion thereof such as a labeled hOAT of this invention) to compete with the test sample hOAT for binding with a limited amount of TBP. The amount of hOAT in the test sample is inversely proportional to the amount of standard that becomes bound to the TBP. To facilitate determining the amount of standard that becomes bound, the TBP generally is insolubilized before or after the competition, so that the standard and analyte that are bound to the TBP conveniently are separated from the standard and analyte which remain unbound.

Sandwich assays involve the use of two TBPs, each capable of binding to a different target portion, or epitope, of hOAT. In a sandwich assay, the test sample analyte is bound by a first TBP which is immobilized on a solid support, and thereafter a second TBP binds to the analyte, thus forming an insoluble three part complex. David & Greene, U.S. Pat. No. 4,376,110. The second antibody may itself be labeled with a detectable moiety (direct sandwich assays) or may be measured using an anti-TBP antibody that is labeled with a detectable moiety (indirect sandwich assay). For example, one type of sandwich assay is an ELISA assay, in which case the detectable moiety is an enzyme.

The TBPs of this invention also are useful for in vivo imaging, wherein a TBP labeled with a detectable moiety is administered to a host, preferably into the bloodstream, and the presence and location of the labeled TBP in the host is assayed.

hOAT nucleic acids or TBPs also can be used in a method for identifying isoforms or alleles of hOAT nucleic acids or polypeptides that place a patient at particular risk for nephrotoxicity. Such variants, alleles or isoforms will exhibit different selectivity towards uptake of certain anions. If these anions are nephrotoxic drugs or drug metabolites, then a patient may be at particular risk of injury. The patient can be tested (e.g., by amplifying genomic hOAT-encoding DNA from a blood sample) to determine if the at-risk variant, isoform or allele is present. If so, then the dosage of the drug can be reduced or an alternative drug used. This method comprises identifying one or more naturally-occurring sequence variations in the human population and determining the selectivity of such variations for transport of a selected nephrotoxic substance. Then a patient is tested for the variation associated with relatively selective transport of the nephrotoxic substance.

Similarly, allelic variation in the transcriptional control regions of the hOAT gene can be analyzed for correlation with susceptibility to uptake and transport of selected nephrotoxic drugs; here the correlation will be with the amount of expression of hOAT as opposed to the selectivity of the hOAT protein. This method comprises identifying one or more naturally-occurring sequence variations in the expression control domain of hOAT in the human population and determining the expression levels of hOAT in cells containing such variant. Patients having relatively high levels of expression of hOAT may not be considered suitable for treatment with nephrotoxic drugs, or the dosage of such drugs may be reduced.

Since at least a domain of hOAT is expressed in the brain as well as the kidney (cf brain EST R25797 and Example 3 below), it is also within the scope of this invention to probe a brain library to obtain the full length gene corresponding to R25797. The sequence of this gene may or may not diverge substantially from the reference sequence hOAT. This notwithstanding, the brain-expressed gene is also a suitable subject for determination of sequence variants such as alleles and isoforms. These may be involved in important neural functions and are suitable subjects for screening to identify them.

hOAT also is useful in screening methods for compounds that can act to suppress or enhance anion uptake and transport by hOAT. Suppression of hOAT activity (antagonism) is useful in reducing the nephrotoxicity of drugs, i.e., to serve as nephroprotective agents, while enhancement of hOAT activity (agonism) is useful in the treatment of kidney dysfunction. The screening methods comprise providing a candidate hOAT agonist or antagonist, contacting the candidate with hOAT nucleic acid or polypeptide, determining the effect of the candidate on the transcription of the hOAT nucleic acid (or the expression or biological activity of the hOAT polypeptide), identifying a hOAT agonist or antagonist, and optionally preparing additional quantities of the agonist or antagonist that is so identified. Biological activity of hOAT is assayed using the stable cell line of Example 1 as shown in Example 2.

hOAT is useful in screening assays for modified forms of heretofore nephrotoxic drugs, or as part of a toxicology screening program to determine the potential nephrotoxicity of new therapeutic compounds. Accumulation of the candidate in hOAT transformants as opposed to control cells is an indicia of potential nephrotoxicity. Determining $CC_{50}$'s using the hOAT transformants would produce a direct measure of potential nephrotoxicity. A candidate form of a suspected compound or a known nephrotoxic drug, e.g., a prodrug, is contacted with the hOAT and its effect on the transport by hOAT of a benchmark anion is determined. Transport of the test compound itself (usually in an isotopically labeled form) also can be determined. Alternatively, transport of the compound in the presence of probenecid can be assayed. If the compound is no longer transported, or the benchmark anion transport is not affected by the compound, or probenecid has no influence on whether or not the compound is transported, then the candidate is suitable for further study in animals as a potential non-nephrotoxic drug, for example, in the case of a prodrug as a non-nephrotoxic form of the parental drug. Prodrugs of nucleotide phosphonate analogues such as cidofovir, PMEA or PMPA suitable for testing include mono and di-esters and amidates of the phosphonyl group.

EXAMPLE 1

Generation of a Cell Line Stably Transformed with hOAT1 Gene

A cell line stably expressing hOAT1 was prepared and characterized to ultimately prove that the isolated cDNA encodes functional hOAT1 protein.

The expression construct containing hOAT1 gene was prepared as follows. hOAT1 coding sequence was PCR amplified from plasmid isolated from human kidney cDNA library. PCR reaction was performed under standard conditions using Expand High Fidelity PCR system (Boehringer Mannheim). Oligonucleotides 5'-ACCGTCTAGAATT CTTTTTATTTTTAATTTTCTTTCAAATACGTCCACCAT GGCCTTTAATGACCTCCTGCAGCAGG-3' (SEQ. ID NO. 3) and 5'-TACTCACGTGGATCCTGATCA-GACGTCTGTAGGACCTTCCCTCCCTTTAGG-3' (SEQ. ID NO. 4) were used as a sense and antisense primer to introduce EcoRI and BamHI restriction site, respectively. In addition, the sense primer contained truncated 5'-untranslated sequence of alfalfa mosaic virus (underlined) and favorable Kozak consensus sequence (CCACCATGG) (SEQ. ID NO.5) to maximize initiation of translation. The PCR product was digested with EcoRI/BamHI and cloned into pIRESneo expression vector (CLONTECH, Palo Alto, Calif.) using the corresponding restriction sites to yield pIRES-hOAT plasmid. After cloning, the correct nucleotide sequence of the whole fragment generated by PCR was verified.

pIRES-hOAT plasmid was transfected into CHO-K1 cells (ATCC CCL61) growing in F-12 nutrient mixture supplemented with 10% fetal bovine serum, 100 U/ml penicillin, and 100 µg/ml streptomycin. 24 hours before transfection, approximately $6 \times 10^6$ CHO-K1 cells were seeded into 100-mm Petri dish. At the time of transfection, media was aspirated and 6 ml of fresh media containing 12 µg of pIRES-hOAT and 60 µg of Cytofectin GSV cationic lipid (Glen Research, Sterling, Va.) was added to the cells. Following overnight incubation, selection of stable transformants started in phenol red-free F-12 nutrient mixture containing fetal bovine serum, penicillin and streptomycin as above, plus 1 mg/ml G418 (CLONTECH). Viable colonies were isolated after 2-week selection and tested for uptake of p-aminohippuric acid (PAH, a prototype substrate of organic anion transport systems) in the presence and absence of probenecid (inhibitor of organic anion transport). For the PAH uptake assay, the cells were seeded into 12-well plates at the density of $2 \times 10^5$ cell/well. After 48 hours, growth media was aspirated and the cells were washed twice with phosphate buffered saline (PBS). The uptake assay was performed in transport buffer (135 mM NaCl, 5 mM KCl, 2.5 mM $CaCl_2$, 1.2 mM $MgCl_2$, 0.8 mM $MgSO_4$, 28 mM glucose, and 13 mM HEPES pH 7.2) containing 5 µM [$^3$H]PAH (New England Nuclear, spec. activity 1.2 Ci/mmol) ±1 mM probenecid. After 90 min incubation at 37° C. in the transport buffer, the cells were washed 3-times with ice-cold PBS (2 ml/well) and lysed directly on the plate in the presence of 0.3% Triton X-100 (0.5 ml/well) for 20 min at room temperature. Plates were washed with additional 0.5 ml/well of Triton X-100, the lysate and wash were combined, scintillation fluid was added, and the radioactivity counted. As a result of this assay, a transformed clone with 30-fold increase in PAH uptake compared to parental CHO-K1 cells was identified and designated CHO-hOAT.

EXAMPLE 2

Functional Characterization of hOAT1

Kinetics of hOAT1-mediated PAH uptake was characterized using CHO-hOAT cells. The uptake assay was performed as described above with various concentrations of [$^3$H]PAH ranging from 5 to 160 µM. To assess net hOAT1-specific uptake, background uptake measured in parental CHO-K1 cells at each substrate concentration was subtracted from that determined in CHO-hOAT cells. Kinetic constants were calculated using Enzyme kinetics software (ChemSW, Fairfield, Calif.). As expected, PAH uptake in CHO-hOAT cells was saturable with $K_m$=13 µM and Vmax=42 pmol/$10^6$ cells. As oppose to the background uptake of PAH in CHO-K1 cells, uptake in CHO-hOAT cells was strongly sensitive to probenecid with $IC_{50}$=6.2 µM when measured at PAH concentration equal to its $K_m$. In addition, PAH accumulation in CHO-hOAT was stimulated approximately 2.5-fold by preloading the cells with 10 mM glutarate indicating that the hOAT protein functions as an organic anion/dicarboxylate exchanger.

EXAMPLE 3

Tissue Distribution of hOAT1

A human multiple tissue Northern blot (CLONTECH) was used for localization of hOAT1 expression in human tissues. A hOAT1-specific [$^{32}$P]dATP labeled probe was generated by random priming the BsrGI/Bsu36I DNA fragment corresponding to nucleotides 420–854 of the hOAT1 coding sequence. The membrane was hybridized for 1 hour at 68° C. in ExpressHyb hybridization buffer (CLONTECH) and then washed twice in 2×SSC with 0.05% SDS for 30 minutes at room temperature followed by a single wash in 0.1×SSC with 0.1% SDS at 50° C. A strong signal was detected in kidney corresponding to a 2.5 kb hOAT1 transcript. No positive signal was found in the other tested tissues (brain, heart, skeletal muscle, colon, thymus, spleen, small intestine, placenta, lung, or peripheral blood leukocytes).

In addition, hOAT1 expression in various human tissues was examined by more sensitive RT-PCR amplification. For this purpose, the Multiple Choice cDNA kits I and II containing tissue specific cDNAs (Origene Technologies, Rockville, Md.) and two sets of hOAT1-specific primers were used for PCR detection of hOAT1 expression. The oligonucleotides, 5'-CCCGCTGGCACTCCTCCTCCGGGAG-3' (SEQ. ID NO. 6) (sense), and 5'-GTAGAGCTCGGCAGTCATGCTCACCA-3' (SEQ. ID NO. 7) (antisense), was used to amplify a 606-bp fragment from the hOAT1 coding region (nucleotides 815–1420). In the independent set of PCR reactions, a 295-bp hOAT1 fragment (comprised of the last 175 coding nucleotides and 120 nucleotides of the 3'-UTR) was amplified using the oligonucleotides, 5'-CCAGCGCTGTCACTGTCCTCCTGC-3' (SEQ. ID NO. 8) (sense), and 5'-AACCCCCACACTTGGGTCACCATTTCCTC-3' (SEQ. ID NO. 9) (antisense). PCR reactions were carried out using the Expand High Fidelity PCR System (Boehringer Mannheim) in a total volume of 25 µl containing 1 µg of tissue-specific cDNA. Thirty-five amplification cycles (95° C. for 40 s, 58° C. for 1 min, and 72° C. for 45 s) were performed. Positive tissues were identified after separation of PCR reactions on a 1% agarose gel. As expected, a strong positive signal was consistently detected in kidney. In contrast with the Northern analysis, brain and skeletal muscle was also positive for hOAT1 expression although to lesser extent compared to kidney.

Presence of hOAT protein in human kidney tissue was verified by an immunoblot analysis with rabbit anti-hOAT1 polyclonal antibody prepared at AnaSpec (San Jose, Calif.) using standard immunological techniques. Briefly, an immunogenic peptide, NH2-TVQDLESRKGKQTR-COOH (SEQ. ID NO. 10), corresponding to hOAT1 amino acids 515–528 was conjugated to keyhole limpet hemocyanine through a cysteine residue added to the peptide's C-terminus. Animal serum was collected after 4 immunizations in the presence of complete Freund's adjuvant and affinity-purified against the immunogenic peptide immobilized on a Sepharose resin. For immunoblot analysis, human kidney cortex was extractracted with a buffer containing 20 mM Tri-HCl, pH 7.5, 150 mM NaCl, 1% NP-40, 0.5% deoxycholate, and 0.1% SDS. After homogenization in the presence of complete proteinase inhibitor cocktail (Boehringer Mannheim) the extract was clarified by high-speed centrifugation, separated by electrophoresis on an 8% SDS-polyacrylamide gel and electroblotted onto a nitrocellulose membrane (Millipore, Bedford, Mass.). The membrane was blocked in PBS/5% dry milk (PBS-M) for 1 hour, washed 3 times in PBS/0.05% Tween 20 (PBS-T), and incubated overnight in PBS-M with the anti-hOAT antibody. Following wash in PBS-T, the membrane was incubated in PBS-M with goat anti-rabbit antibody conjugated to horseradish peroxidase (Zymed, South San Francisco, Calif.). After an additional wash and incubation with a chemiluminescent substrate (Amersham, Arligton Heights, Ill.), the immunoblot was exposed to X-ray film. The antibody recognized a heterogeneous product with an apparent molecular weight of 80 to 90 kDa. This was significantly larger than the predicted molecular weight from the hOAT1 amino acid sequence (60.3 kDa). However, when the cortex extract was treated with peptide:N-glycosidase F, which specifically cleaves N-linked oligosaccharide chains, a homogeneous product of 60 kDa was detected on the immunoblot.

EXAMPLE 4

Determination of Nephrotoxic Potential by Cell Culture Assay Using hOAT Transformants Adefovir (ADV) is an anti-HIV nucleotide analog with unique resistance profile currently undergoing Phase III clinical evaluation. The most important clinical toxicity of ADV is nephrotoxicity associated with changes in laboratory markers of renal functions. ADV is a substrate for human renal organic anion transporter 1 (hOAT) located in the basolateral membrane of the proximal convoluted tubules. In this example, the role of hOAT in the mechanism of ADV nephrotoxicity was investigated.

Chinese hamster ovary cells (CHO), which exhibit low sensitivity to ADV cytotoxicity due to its limited uptake, were stably transformed with hOAT cDNA to generate CHO-hOAT cells as described above. Uptake and cytotoxicity of ADV in the two cell lines was compared.

CHO-hOAT accumulated ADV to levels >300-fold higher compared to CHO. Uptake of ADV by CHO-hOAT was saturable ($K_m$=23 uM, $V_{max}$=390 pmol/$10^6$ cells) and sensitive to the hOAT inhibitor probenecid (PBC; $IC_{50}$=6.5 uM). Importantly, ADV was ~500-fold more cytotoxic in CHO-hOAT compared to CHO cells. However, in the presence of 1 mM PBC, CHO-hOAT were only 3-fold more susceptible to ADV than were CHO. Another antiviral nucleotide, cidofovir (CDV), but not its cyclic prodrug (cCDV), also efficiently accumulated in CHO-hOAT ($K_m$=70 uM, $V_{max}$=1,110 pmol/$10^6$ cells). Accordingly, CDV was >400-fold more cytotoxic in CHO-hOAT compared to CHO. In contrast, cytotoxicity of cCDV was increased to much lesser extent in CHO-hOAT cells corresponding with the lack of cCDV nephrotoxicity. Similar to ADV, CDV cytotoxicity was also significantly reduced by PBC.

Expression of hOAT enhances cytotoxicity of ADV. Since high-level expression of hOAT is specific to renal tubules, hOAT plays a crucial role in the mechanism of ADV nephrotoxicity. Thus, hOAT inhibitors (e.g. PBC) may be useful to overcome ADV nephrotoxicity. Observations with CDV and cCDV correlate with their nephrotoxic potential and provide additional support for the involvement of hOAT in this process.

What is claimed is:

1. An isolated hOAT polypeptide having the sequence of SEQ. ID. NO. 2.

\* \* \* \* \*

SEQUENCE LISTING

```
<160> NUMBER OF SEQ ID NOS: 10

<210> SEQ ID NO 1
<211> LENGTH: 2123
<212> TYPE: DNA
<213> ORGANISM: Homo sapiens
<220> FEATURE:
<221> NAME/KEY: CDS
<222> LOCATION: (263)..(1912)

<400> SEQUENCE: 1
ttcctgccct gacccccaaa gtgaggagaa gctgcaaggg aaaagggagg gacagatcag      60
ggagaccggg gaagaaggag gacgagccaa ggaggctgct gtcccccac agagcagctc     120 ggactcagct cccgggaagc aacccagctg cggaggcaac ggcagtgctg ctcctccagc     180
gaaggacagc aggcaggcag acagacagag gtcctgggac tggaaggcct cagcccccag    240
```

-continued

| | |
|---|---|
| ccactgggct gggcctggcc ca atg gcc ttt aat gac ctc ctg cag cag gtg<br>                                   Met Ala Phe Asn Asp Leu Leu Gln Gln Val<br>                                    1           5                 10 | 292 |
| ggg ggt gtc ggc cgc ttc cag cag atc cag gtc acc ctg gtg gtc ctc<br>Gly Gly Val Gly Arg Phe Gln Gln Ile Gln Val Thr Leu Val Val Leu<br>             15                 20                  25 | 340 |
| ccc ctg ctc ctg atg gct tct cac aac acc ctg cag aac ttc act gct<br>Pro Leu Leu Leu Met Ala Ser His Asn Thr Leu Gln Asn Phe Thr Ala<br>         30                 35                  40 | 388 |
| gcc atc cct acc cac cac tgc cgc ccg cct gcc gat gcc aac ctc agc<br>Ala Ile Pro Thr His His Cys Arg Pro Pro Ala Asp Ala Asn Leu Ser<br>        45                 50                 55 | 436 |
| aag aac ggg ggg ctg gag gtc tgg ctg ccc cgg gac agg cag ggg cag<br>Lys Asn Gly Gly Leu Glu Val Trp Leu Pro Arg Asp Arg Gln Gly Gln<br>60                 65                 70 | 484 |
| cct gag tcc tgc ctc cgc ttc acc tcc ccg cag tgg gga ctg ccc ttt<br>Pro Glu Ser Cys Leu Arg Phe Thr Ser Pro Gln Trp Gly Leu Pro Phe<br>75                 80                 85                 90 | 532 |
| ctc aat ggc aca gaa gcc aat ggc aca ggg gcc aca gag ccc tgc acc<br>Leu Asn Gly Thr Glu Ala Asn Gly Thr Gly Ala Thr Glu Pro Cys Thr<br>                 95                 100              105 | 580 |
| gat ggc tgg atc tat gac aac agc acc ttc cca tct acc atc gtg act<br>Asp Gly Trp Ile Tyr Asp Asn Ser Thr Phe Pro Ser Thr Ile Val Thr<br>                 110                115              120 | 628 |
| gag tgg gac ctt gtg tgc tct cac agg gcc cta cgc cag ctg gcc cag<br>Glu Trp Asp Leu Val Cys Ser His Arg Ala Leu Arg Gln Leu Ala Gln<br>               125                130              135 | 676 |
| tcc ttg tac atg gtg ggg gtg ctc ctc gga gcc atg gtg ttc ggc tac<br>Ser Leu Tyr Met Val Gly Val Leu Leu Gly Ala Met Val Phe Gly Tyr<br>        140                 145                150 | 724 |
| ctt gca gac agg cta ggc cgc cgg aag gta ctc atc ttg aac tac ctg<br>Leu Ala Asp Arg Leu Gly Arg Arg Lys Val Leu Ile Leu Asn Tyr Leu<br>155                160              165              170 | 772 |
| cag aca gct gtg tca ggg acc tgc gca gcc ttc gca ccc aac ttc ccc<br>Gln Thr Ala Val Ser Gly Thr Cys Ala Ala Phe Ala Pro Asn Phe Pro<br>                175                180              185 | 820 |
| atc tac tgc ttc cgg ctc ctc tcg ggc atg gct ctg gct ggc atc<br>Ile Tyr Cys Ala Phe Arg Leu Leu Ser Gly Met Ala Leu Ala Gly Ile<br>               190                195              200 | 868 |
| tcc ctc aac tgc atg aca ctg aat gtg gag tgg atg ccc att cac aca<br>Ser Leu Asn Cys Met Thr Leu Asn Val Glu Trp Met Pro Ile His Thr<br>        205                 210                215 | 916 |
| cgg gcc tgc gtg ggc acc ttg att ggc tat gtc tac agc ctg ggc cag<br>Arg Ala Cys Val Gly Thr Leu Ile Gly Tyr Val Tyr Ser Leu Gly Gln<br>220                225              230 | 964 |
| ttc ctc ctg gct ggt gtg gcc tac gct gtg ccc cac tgg cgc cac ctg<br>Phe Leu Leu Ala Gly Val Ala Tyr Ala Val Pro His Trp Arg His Leu<br>235                240              245              250 | 1012 |
| cag cta ctg gtc tct gcg cct ttt ttt gcc ttc ttc atc tac tcc tgg<br>Gln Leu Leu Val Ser Ala Pro Phe Phe Ala Phe Phe Ile Tyr Ser Trp<br>                255                260              265 | 1060 |
| ttc ttc att gag tcg gcc cgc tgg cac tcc tcc tcc ggg agg ctg gac<br>Phe Phe Ile Glu Ser Ala Arg Trp His Ser Ser Ser Gly Arg Leu Asp<br>               270                275              280 | 1108 |
| ctc acc ctg agg gcc ctg cag aga gtc gcc cgg atc aat ggg aag cgg<br>Leu Thr Leu Arg Ala Leu Gln Arg Val Ala Arg Ile Asn Gly Lys Arg<br>        285                 290                295 | 1156 |
| gaa gaa gga gcc aaa ttg agt atg gag gta ctc cgg gcc agt ctg cag<br>Glu Glu Gly Ala Lys Leu Ser Met Glu Val Leu Arg Ala Ser Leu Gln<br>300                305              310 | 1204 |

-continued

```
aag gag ctg acc atg ggc aaa ggc cag gca tcg gcc atg gag ctg ctg     1252
Lys Glu Leu Thr Met Gly Lys Gly Gln Ala Ser Ala Met Glu Leu Leu
315                 320                 325                 330 cgc tgc ccc acc ctc cgc cac ctc ttc ctc tgc ctc tcc atg ctg tgg     1300
Arg Cys Pro Thr Leu Arg His Leu Phe Leu Cys Leu Ser Met Leu Trp
            335                 340                 345 ttt gcc act agc ttt gca tac tat ggg ctg gtc atg gac ctg cag ggc     1348
Phe Ala Thr Ser Phe Ala Tyr Tyr Gly Leu Val Met Asp Leu Gln Gly
        350                 355                 360 ttt gga gtc agc atc tac cta atc cag gtg atc ttt ggt gct gtg gac     1396
Phe Gly Val Ser Ile Tyr Leu Ile Gln Val Ile Phe Gly Ala Val Asp
    365                 370                 375 ctg cct gcc aag ctt gtg ggc ttc ctt gtc atc aac tcc ctg ggt cgc     1444
Leu Pro Ala Lys Leu Val Gly Phe Leu Val Ile Asn Ser Leu Gly Arg
380                 385                 390 cgg cct gcc cag atg gct gca ctg ctg ctg gca ggc atc tgc atc ctg     1492
Arg Pro Ala Gln Met Ala Ala Leu Leu Leu Ala Gly Ile Cys Ile Leu
395                 400                 405                 410 ctc aat ggg gtg ata ccc cag gac cag tcc att gtc cga acc tct ctt     1540
Leu Asn Gly Val Ile Pro Gln Asp Gln Ser Ile Val Arg Thr Ser Leu
            415                 420                 425 gct gtg ctg ggg aag ggt tgt ctg gct gcc tcc ttc aac tgc atc ttc     1588
Ala Val Leu Gly Lys Gly Cys Leu Ala Ala Ser Phe Asn Cys Ile Phe
        430                 435                 440 ctc tat act ggg gaa ctg tat ccc aca atg atc cgg cag aca ggc atg     1636
Leu Tyr Thr Gly Glu Leu Tyr Pro Thr Met Ile Arg Gln Thr Gly Met
    445                 450                 455 gga atg ggc agc acc atg gcc cga gtg ggc agc atc gtg agc cca ctg     1684
Gly Met Gly Ser Thr Met Ala Arg Val Gly Ser Ile Val Ser Pro Leu
460                 465                 470 gtg agc atg act gcc gag ctc tac ccc tcc atg cct ctc ttc atc tac     1732
Val Ser Met Thr Ala Glu Leu Tyr Pro Ser Met Pro Leu Phe Ile Tyr
475                 480                 485                 490 ggt gct gtt cct gtg gcc gcc agc gct gtc act gtc ctc ctg cca gag     1780
Gly Ala Val Pro Val Ala Ala Ser Ala Val Thr Val Leu Leu Pro Glu
            495                 500                 505 acc ctg ggc cag cca ctg cca gac acg gtg cag gac ctg gag agc agg     1828
Thr Leu Gly Gln Pro Leu Pro Asp Thr Val Gln Asp Leu Glu Ser Arg
        510                 515                 520 aaa ggg aaa cag acg cga cag caa caa gag cac cag aag tat atg gtc     1876
Lys Gly Lys Gln Thr Arg Gln Gln Gln Glu His Gln Lys Tyr Met Val
    525                 530                 535 cca ctg cag gcc tca gca caa gag aag aat gga ctc tgaggactga          1922
Pro Leu Gln Ala Ser Ala Gln Glu Lys Asn Gly Leu
540                 545                 550 gaagggcct tacagaaccc taaagggagg aaggtccta caggtctccg gccacccaca     1982
caaggaggag gaagaggaaa tggtgaccca agtgtggggg ttgtggttca ggaaagcatc   2042
ttcccagggg tccacctccc tttataaacc ccaccagaac cacatcatta aaggtttga   2102 ctgcgaaaaa aaaaaaaaaa a                                             2123
```

<210> SEQ ID NO 2
<211> LENGTH: 550
<212> TYPE: PRT
<213> ORGANISM: Homo sapiens

<400> SEQUENCE: 2

```
Met Ala Phe Asn Asp Leu Leu Gln Gln Val Gly Gly Val Gly Arg Phe
1               5                   10                  15
```

-continued

```
Gln Gln Ile Gln Val Thr Leu Val Leu Pro Leu Leu Met Ala
         20                  25                  30

Ser His Asn Thr Leu Gln Asn Phe Thr Ala Ala Ile Pro Thr His His
         35                  40                  45

Cys Arg Pro Ala Asp Ala Asn Leu Ser Lys Asn Gly Gly Leu Glu
 50                  55                  60

Val Trp Leu Pro Arg Asp Arg Gln Gly Gln Pro Glu Ser Cys Leu Arg
 65                  70                  75                  80

Phe Thr Ser Pro Gln Trp Gly Leu Pro Phe Leu Asn Gly Thr Glu Ala
                 85                  90                  95

Asn Gly Thr Gly Ala Thr Glu Pro Cys Thr Asp Gly Trp Ile Tyr Asp
             100                 105                 110

Asn Ser Thr Phe Pro Ser Thr Ile Val Thr Glu Trp Asp Leu Val Cys
         115                 120                 125

Ser His Arg Ala Leu Arg Gln Leu Ala Gln Ser Leu Tyr Met Val Gly
     130                 135                 140

Val Leu Leu Gly Ala Met Val Phe Gly Tyr Leu Ala Asp Arg Leu Gly
145                 150                 155                 160

Arg Arg Lys Val Leu Ile Leu Asn Tyr Leu Gln Thr Ala Val Ser Gly
                165                 170                 175

Thr Cys Ala Ala Phe Ala Pro Asn Phe Pro Ile Tyr Cys Ala Phe Arg
            180                 185                 190

Leu Leu Ser Gly Met Ala Leu Ala Gly Ile Ser Leu Asn Cys Met Thr
        195                 200                 205

Leu Asn Val Glu Trp Met Pro Ile His Thr Arg Ala Cys Val Gly Thr
    210                 215                 220

Leu Ile Gly Tyr Val Tyr Ser Leu Gly Gln Phe Leu Leu Ala Gly Val
225                 230                 235                 240

Ala Tyr Ala Val Pro His Trp Arg His Leu Gln Leu Leu Val Ser Ala
                245                 250                 255

Pro Phe Phe Ala Phe Phe Ile Tyr Ser Trp Phe Phe Ile Glu Ser Ala
            260                 265                 270

Arg Trp His Ser Ser Ser Gly Arg Leu Asp Leu Thr Leu Arg Ala Leu
        275                 280                 285

Gln Arg Val Ala Arg Ile Asn Gly Lys Arg Glu Glu Gly Ala Lys Leu
    290                 295                 300

Ser Met Glu Val Leu Arg Ala Ser Leu Gln Lys Glu Leu Thr Met Gly
305                 310                 315                 320

Lys Gly Gln Ala Ser Ala Met Glu Leu Leu Arg Cys Pro Thr Leu Arg
                325                 330                 335

His Leu Phe Leu Cys Leu Ser Met Leu Trp Phe Ala Thr Ser Phe Ala
            340                 345                 350

Tyr Tyr Gly Leu Val Met Asp Leu Gln Gly Phe Gly Val Ser Ile Tyr
        355                 360                 365

Leu Ile Gln Val Ile Phe Gly Ala Val Asp Leu Pro Ala Lys Leu Val
    370                 375                 380

Gly Phe Leu Val Ile Asn Ser Leu Gly Arg Arg Pro Ala Gln Met Ala
385                 390                 395                 400

Ala Leu Leu Leu Ala Gly Ile Cys Ile Leu Leu Asn Gly Val Ile Pro
                405                 410                 415

Gln Asp Gln Ser Ile Val Arg Thr Ser Leu Ala Val Leu Gly Lys Gly
            420                 425                 430
```

```
Cys Leu Ala Ala Ser Phe Asn Cys Ile Phe Leu Tyr Thr Gly Glu Leu
        435                 440                 445

Tyr Pro Thr Met Ile Arg Gln Thr Gly Met Gly Met Gly Ser Thr Met
    450                 455                 460

Ala Arg Val Gly Ser Ile Val Ser Pro Leu Val Ser Met Thr Ala Glu
465                 470                 475                 480

Leu Tyr Pro Ser Met Pro Leu Phe Ile Tyr Gly Ala Val Pro Val Ala
                485                 490                 495

Ala Ser Ala Val Thr Val Leu Leu Pro Glu Thr Leu Gly Gln Pro Leu
            500                 505                 510

Pro Asp Thr Val Gln Asp Leu Glu Ser Arg Lys Gly Lys Gln Thr Arg
                515                 520                 525

Gln Gln Gln Glu His Gln Lys Tyr Met Val Pro Leu Gln Ala Ser Ala
            530                 535                 540

Gln Glu Lys Asn Gly Leu
545                 550

<210> SEQ ID NO 3
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
accgtctaga attctttta tttttaattt tctttcaaat acgtccacca tggcctttaa      60
tgacctcctg cagcagg                                                   77

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tactcacgtg gatcctgatc agacgtctgt aggaccttcc ctcccttag g               51

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence: Kozak
      consensus sequence

<400> SEQUENCE: 5 ccaccatgg                                                             9

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cccgctggca ctcctcctcc gggag                                           25
```

```
<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtagagctcg gcagtcatgc tcacca                                          26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccagcgctgt cactgtcctc ctgc                                            24

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 aaccccaca cttgggtcac catttcctc                                        29

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 10

Thr Val Gln Asp Leu Glu Ser Arg Lys Gly Lys Gln Thr Arg
 1               5                  10
```